US012186629B2

(12) United States Patent
Nakamura et al.

(10) Patent No.: US 12,186,629 B2
(45) Date of Patent: Jan. 7, 2025

(54) WALKING TRAINING SYSTEM WITH INCREASED WALKING STATE ACCURACY, CONTROL METHOD THEREOF, AND CONTROL PROGRAM

(71) Applicant: TOYOTA JIDOSHA KABUSHIKI KAISHA, Toyota (JP)

(72) Inventors: Takuma Nakamura, Nisshin (JP); Kazuhiro Shintani, Toyokawa (JP); Taiga Matsumoto, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 448 days.

(21) Appl. No.: 17/654,495

(22) Filed: Mar. 11, 2022

(65) Prior Publication Data

US 2022/0331664 A1 Oct. 20, 2022

(30) Foreign Application Priority Data

Apr. 15, 2021 (JP) ................................. 2021-069172

(51) Int. Cl.
*A63B 24/00* (2006.01)
*A61H 1/02* (2006.01)
*A61H 3/00* (2006.01)
*A63B 22/02* (2006.01)

(52) U.S. Cl.
CPC ....... *A63B 24/0087* (2013.01); *A61H 1/0262* (2013.01); *A61H 3/008* (2013.01); *A63B 22/02* (2013.01); *A63B 24/0062* (2013.01); *A61H 2003/007* (2013.01); *A63B 2220/52* (2013.01); *A63B 2220/833* (2013.01)

(58) Field of Classification Search
None
See application file for complete search history.

(56) References Cited

U.S. PATENT DOCUMENTS

| 9,782,659 B2* | 10/2017 | Yamazaki | .......... A63B 24/0062 |
| 10,045,904 B2* | 8/2018 | Takashima | ......... A63B 69/0062 |
| 2015/0173652 A1 | 6/2015 | Brunner | |

(Continued)

FOREIGN PATENT DOCUMENTS

| JP | 2015107247 A | 6/2015 |
| JP | 2016073525 A | 5/2016 |

(Continued)

*Primary Examiner* — John E Breene
*Assistant Examiner* — Nigel H Plumb
(74) *Attorney, Agent, or Firm* — Dickinson Wright, PLLC

(57) ABSTRACT

A walking training system according to the present embodiment includes: a treadmill; a load distribution sensor that is provided on a lower side of a belt of the treadmill so as not to move together with the belt and that detects a distribution of a load received from a sole of a trainee riding on the belt of the treadmill; an extraction unit that extracts a load distribution in a region corresponding to a position of the sole of the trainee during walking training, out of a load distribution detected by the load distribution sensor; and a determination unit that determines a walking state of the trainee based on the load distribution extracted by the extraction unit. A walking training system according to the present application provides improved training to a trainee by improving the accuracy of determining the walking state of the trainee.

8 Claims, 9 Drawing Sheets

(56) References Cited

U.S. PATENT DOCUMENTS

| | | |
|---|---|---|
| 2016/0158622 A1 | 6/2016 | Yamazaki |
| 2017/0065478 A1 | 3/2017 | Takashima |
| 2021/0005319 A1* | 1/2021 | Otsuki .................. G16H 40/40 |

FOREIGN PATENT DOCUMENTS

| | | |
|---|---|---|
| JP | 2016106951 A | 6/2016 |
| JP | 2017051427 A | 3/2017 |
| JP | 2019118706 A | 7/2019 |

* cited by examiner (S103)

(S105)

(S106)

WALKING TRAINING SYSTEM WITH INCREASED WALKING STATE ACCURACY, CONTROL METHOD THEREOF, AND CONTROL PROGRAM

CROSS-REFERENCE TO RELATED APPLICATION

This application claims priority to Japanese Patent Application No. 2021-069172 filed on Apr. 15, 2021, incorporated herein by reference in its entirety.

BACKGROUND

1. Technical Field

The present disclosure relates to a walking training system, a control method thereof, and a control program.

2. Description of Related Art

Japanese Unexamined Patent Application Publication No. 2016-73525 (JP 2016-73525 A) discloses a walking training system including a dynamic balance ability evaluation device for evaluating a dynamic balance ability of a user based on changes over time of a predetermined body part due to walking of the user, and a treadmill for the user to perform walking training. This walking training system includes a pressure sensor on the belt of the treadmill, and detects the force with which the user kicks the belt (floor reaction force) from the measured value of the pressure sensor, for example.

SUMMARY

The response performance of the pressure sensor when the pressure sensor is unloaded is usually lower than that when the pressure sensor is loaded. Therefore, in the related art, when the load distribution received from the sole of the user (trainee) moves with the movement of the belt, not only the load distribution after the movement is detected but also the load distribution before the movement is unintentionally detected without being removed. Therefore, the related art cannot accurately determine the walking state of the user and cannot provide the user with effective walking training.

The present disclosure has been made in view of the above background, and an object of the present disclosure is to provide a walking training system capable of providing effective training to a trainee by improving accuracy of determining the walking state of the trainee, a control method thereof, and a control program.

A walking training system according to an embodiment of the present disclosure includes: a treadmill; a load distribution sensor that is provided on a lower side of a belt of the treadmill so as not to move together with the belt and that detects a distribution of a load received from a sole of a trainee riding on the belt of the treadmill; an extraction unit that extracts a load distribution in a region corresponding to a position of the sole of the trainee during walking training, out of a load distribution detected by the load distribution sensor; and a determination unit that determines a walking state of the trainee based on the load distribution extracted by the extraction unit. This walking training system can suppress the influence of the load distribution that is detected unintentionally due to the low response performance of the load distribution sensor when the load distribution sensor is unloaded. Therefore, it is possible to improve the accuracy of determining the walking state of the trainee, and as a result, it is possible to provide the trainee with effective walking training.

The extraction unit extracts a load distribution in a range of a sole size of the trainee, out of the load distribution detected by the load distribution sensor, the extracted load distribution including a load at a rear end of a load distribution extending in a moving direction of the belt of the treadmill. Here, the sole size of the trainee includes at least one of an area, a length, and a width of the sole and is registered in advance in a database.

The extraction unit specifies the position of the sole of the trainee from an outer edge shape at a rear end of a load distribution extending in a moving direction of the belt of the treadmill, and extracts a load distribution in a region corresponding to the specified position of the sole. Here, the extraction unit specifies the position of the sole of the trainee during walking training by matching part of a shape of the sole of the trainee registered in advance in a database with the outer edge shape.

The walking training system further includes an imaging device for capturing an image of the trainee during walking training, wherein the extraction unit specifies the position of the sole of the trainee during walking training from the image captured by the imaging device, and extracts a load distribution in a region corresponding to the specified position of the sole.

A method for controlling a walking training system according to an embodiment of the present disclosure includes: a step of using a load distribution sensor that is provided on a lower side of a belt of a treadmill so as not to move together with the belt, to detect a distribution of a load received from a sole of a trainee riding on the belt of the treadmill; a step of extracting a load distribution in a region corresponding to a position of the sole of the trainee during walking training, out of a load distribution detected by the load distribution sensor; and a step of determining a walking state of the trainee based on the extracted load distribution. The method for controlling a walking training system can suppress the influence of the load distribution that is detected unintentionally due to the low response performance of the load distribution sensor when the load distribution sensor is unloaded. Therefore, it is possible to improve the accuracy of determining the walking state of the trainee, and as a result, it is possible to provide the trainee with effective walking training.

A control program according to an embodiment of the present disclosure causes a computer to execute: a process of using a load distribution sensor that is provided on a lower side of a belt of a treadmill so as not to move together with the belt, to detect a distribution of a load received from a sole of a trainee riding on the belt of the treadmill; a process of extracting a load distribution in a region corresponding to a position of the sole of the trainee during walking training, out of a load distribution detected by the load distribution sensor; and a process of determining a walking state of the trainee based on the extracted load distribution. This control program can suppress the influence of the load distribution that is detected unintentionally due to the low response performance of the load distribution sensor when the load distribution sensor is unloaded. Therefore, it is possible to improve the accuracy of determining the walking state of the trainee, and as a result, it is possible to provide the trainee with effective walking training.

According to the present disclosure, it is possible to provide a walking training system capable of providing effective training to a trainee by improving accuracy of determining the walking state of the trainee, a control method thereof, and a control program.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Hereinafter, the present disclosure will be described through embodiments of the disclosure, but the disclosure according to the scope of the claims is not limited to the following embodiments. Moreover, not all of the configurations described in the embodiments are indispensable as means for solving the problem. For the sake of clarity, omission and simplification are made as appropriate in the following description and drawings. In each drawing, the same elements are designated by the same reference signs, and duplicate descriptions are omitted as necessary.

First Embodiment

Figure 1:
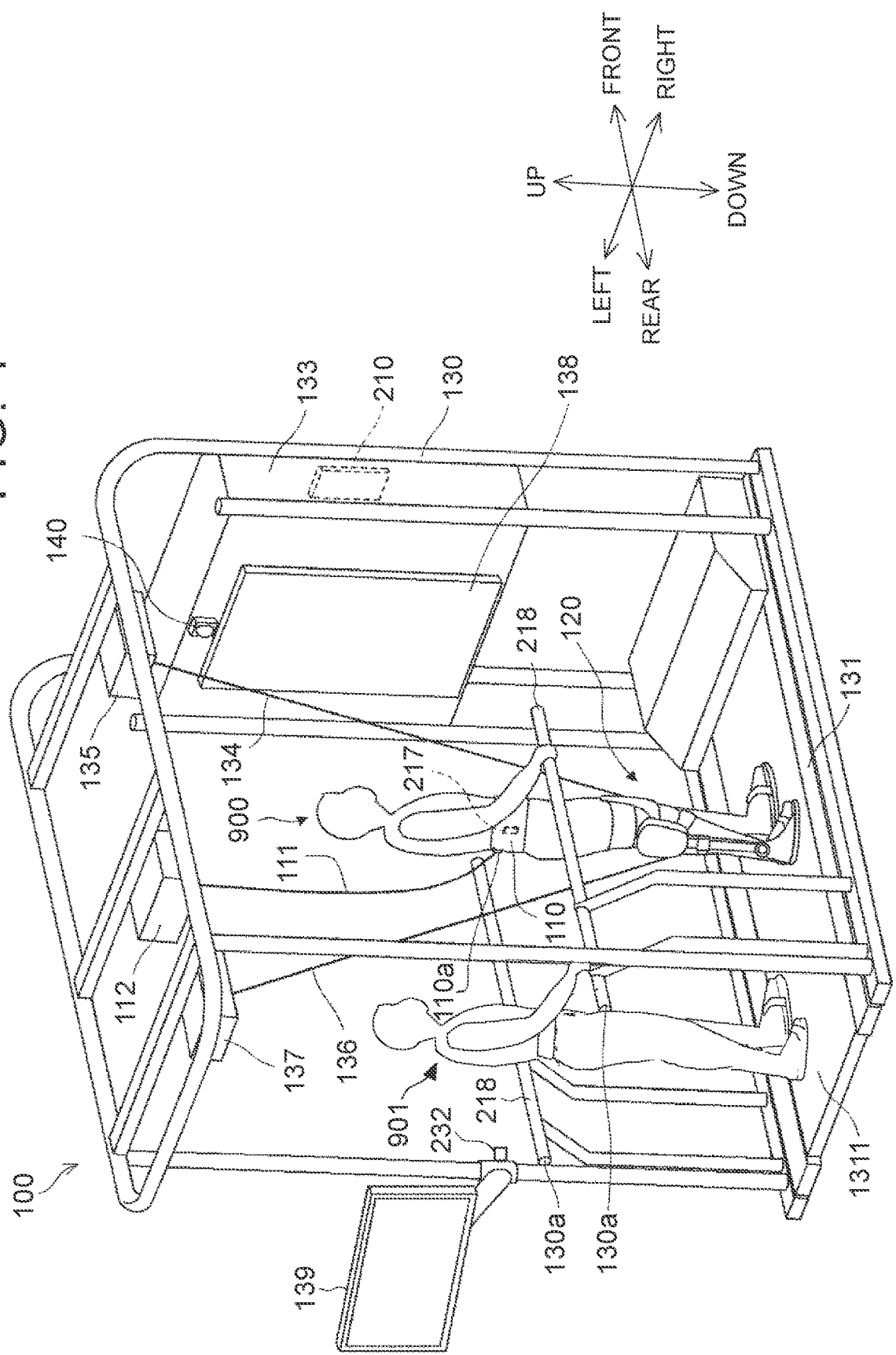
FIG. 1 is an overall conceptual diagram showing a configuration example of a walking training device according to a first embodiment.

FIG. 1 is an overall conceptual diagram showing a configuration example of a walking training device according to a first embodiment. A walking training device 100 according to the present embodiment is a specific example of a rehabilitation support device that supports the rehab (rehabilitation) of a trainee (user) 900, and is particularly a specific example of a walking training device that supports walking training. The walking training device 100 is a device for the trainee 900 who is a hemiplegic patient suffering from paralysis in one leg to perform walking training in accordance with the guidance of a training staff 901. Here, the training staff 901 can be, for example, a therapist (physiotherapist) or a doctor, and assists the training of the trainee by guidance or caregiving. Therefore, the training staff 901 may be called a training instructor, a training caregiver, or a training assistant. The walking training device 100 can also be called a walking training system. The up-down direction, the right-left direction and the front-rear direction in the following description are directions based on the direction of the trainee 900.

The walking training device 100 mainly includes a control panel 133 attached to a frame 130 constituting the entire skeleton, a treadmill 131 on which the trainee 900 walks, and a walking assist device (robot leg) 120 that is attached to an affected leg that is a leg of the trainee 900 on the paralyzed side.

The treadmill 131 is a device that prompts the trainee 900 to walk, and the trainee 900 who performs walking training rides on a belt 1311 and attempts a walking motion in accordance with the movement of the belt 1311. As shown in FIG. 1, the training staff 901 can stand on the belt 1311 behind the trainee 900 and perform a walk motion together with the trainee 900. However, it is usually preferable that the training staff 901 be in a state in which it is easy to perform caregiving to the trainee 900, that is, standing over the belt 1311, for example.

Figure 2:
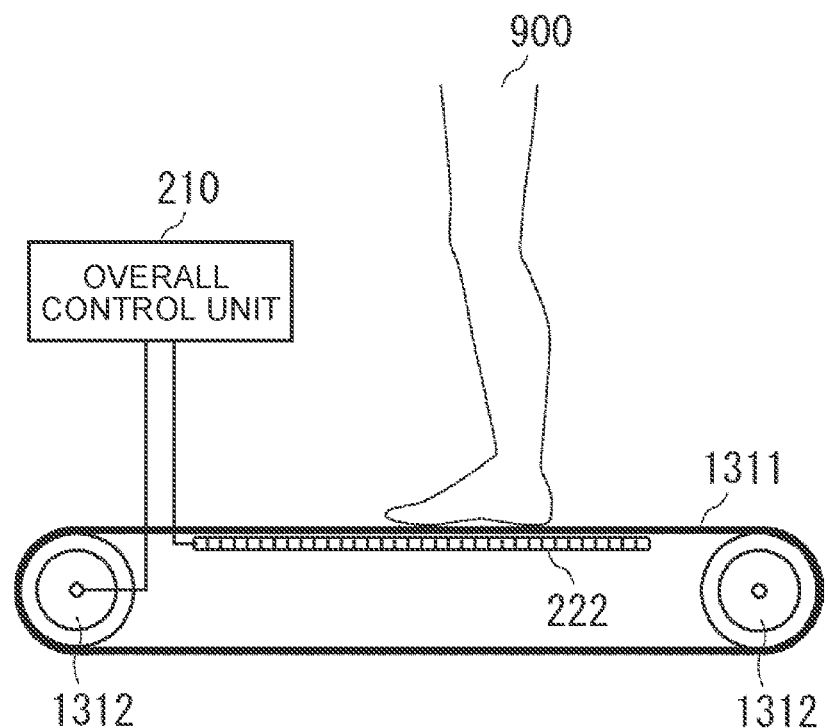
FIG. 2 is a schematic side view of a part of a treadmill provided in the walking training device shown in FIG. 1.
Figure 2:
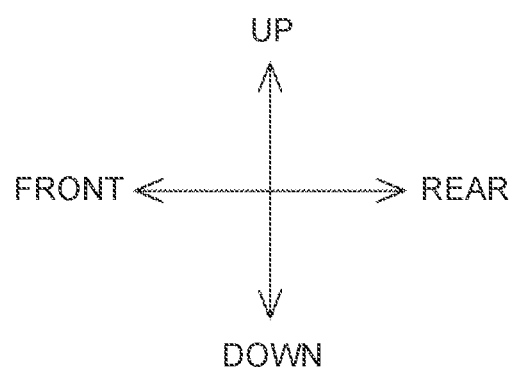

FIG. 2 is a schematic side view of a part of the treadmill 131. As shown in FIG. 2, the treadmill 131 includes at least the ring-shaped belt 1311, a pulley 1312, and a motor (not shown). Further, a load distribution sensor 222 is installed on the inner side of the belt 1311 (on the lower side of the belt 1311 on the surface of which the trainee 900 rides) so as not to move together with the belt 1311.

The load distribution sensor 222 is composed of a plurality of sensors, and these sensors are arranged in a matrix on the lower side of the belt 1311 that supports the sole of the trainee 900. By using these sensors, the load distribution sensor 222 can detect the magnitude and the distribution of the surface pressure (load) received from the sole of the trainee 900. For example, the load distribution sensor 222 is a resistance change detection-type load detection sheet in which a plurality of electrodes is arranged in a matrix. From the detection result of the load distribution sensor 222, it is possible to determine the walking state of the trainee 900 (whether each leg is in a standing state or a swinging state, and the like). The details of the method of determining the walking state of the trainee 900 based on the detection result of the load distribution sensor 222 will be described later.

In the treadmill 131, for example, an overall control unit 210, which will be described later, determines the walking state of the trainee 900 based on the detection result of the load distribution sensor 222, and uses a motor (not shown) to rotate the pulley 1312 in accordance with the walking state, thereby rotating (moving) the ring-shaped belt 1311. As a result, the trainee 900 can perform walking training without stepping out from the belt 1311.

The frame 130 stands on the treadmill 131 installed on the floor surface, and supports the control panel 133 that houses the overall control unit 210 that controls the motor and the sensor and supports a training monitor 138 that is, for example, a liquid crystal panel that presents the training progress and the like to the trainee 900. Further, the frame 130 supports a front tension portion 135 near the front of the overhead portion of the trainee 900, a harness tension portion 112 near the overhead portion, and a rear tension portion 137 near the rear of the overhead portion. The frame 130 also includes handrails 130a for the trainee 900 to grab.

The handrails 130a are arranged on right and left sides of the trainee 900. Each handrail 130a is disposed to extend in a direction parallel to the walking direction of the trainee 900. The position of the handrail 130a in the up-down direction and the right-left direction can be adjusted. That is, the handrail 130a can include a mechanism for changing its height and width. Further, the handrail 130a can be configured such that the height of the handrail 130a is adjusted to make the height of the front side and the height of the rear side in the walking direction different so as to change the inclination angle thereof, for example. For example, the handrail 130a can be provided with an inclination angle that gradually increases along the walking direction.

Further, the handrail 130a is provided with a handrail sensor 218 for detecting the load received from the trainee 900. For example, the handrail sensor 218 can be a resistance change detection-type load detection sheet in which electrodes are arranged in a matrix. Further, the handrail sensor 218 can be a six-axis sensor in which a three-axis acceleration sensor (x, y, z) and a three-axis gyro sensor (roll, pitch, yaw) are combined. However, the type and the installation position of the handrail sensor 218 are not limited.

A camera 140 functions as an imaging unit for observing the whole body of the trainee 900. The camera 140 is installed near the training monitor 138 so as to face the trainee. The camera 140 captures still images and moving images of the trainee 900 during training. The camera 140 includes a set of a lens and an imaging element that provides such an angle of view that the whole body of the trainee 900 can be captured. The imaging element is, for example, a complementary metal-oxide-semiconductor (CMOS) image sensor that converts an optical image formed on an image plane into an image signal.

With the coordinated operation of the front tension portion 135 and the rear tension portion 137, the load of the walking assist device 120 is offset so as not to be a burden on the affected leg, and further, the forward swing motion of the affected leg is assisted in accordance with the degree of the setting.

One end of a front wire 134 is connected to a winding mechanism of the front tension portion 135, and the other end is connected to the walking assist device 120. The winding mechanism of the front tension portion 135 winds and unwinds the front wire 134 in accordance with the movement of the affected leg by turning on and off a motor (not shown). Similarly, one end of a rear wire 136 is connected to a winding mechanism of the rear tension portion 137, and the other end is connected to the walking assist device 120. The winding mechanism of the rear tension portion 137 winds and unwinds the rear wire 136 in accordance with the movement of the affected leg by turning on and off a motor (not shown). With such a coordinated operation of the front tension portion 135 and the rear tension portion 137, the load of the walking assist device 120 is offset so as not to be a burden on the affected leg, and further, the forward swing motion of the affected leg is assisted in accordance with the degree of the setting.

For example, as an operator, the training staff 901 sets the level of assistance to high, for a trainee who has severe paralysis. When the assist level is set to high, the front tension portion 135 winds up the front wire 134 with a relatively large force in accordance with the forward swing timing of the affected leg. As the training progresses and assistance becomes no longer needed, the training staff 901 sets the assist level to the minimum. When the assist level is set to the minimum, the front tension portion 135 winds up the front wire 134 with a force to cancel the weight of the walking assist device 120 in accordance with the forward swing timing of the affected leg.

The walking training device 100 further includes a fall prevention harness device composed of a brace 110, a harness wire 111, and a harness tension portion 112.

The brace 110 is a belt wrapped around the abdomen of the trainee 900 and is fixed to the waist portion by, for example, a hook-and-loop fastener. The brace 110 includes a connecting hook 110a for connecting one end of the harness wire 111 that is a hanger, and can also be referred to as a hanger belt. The trainee 900 wears the brace 110 such that the connecting hook 110a is located on the rear back portion.

One end of the harness wire 111 is connected to the connecting hook 110a of the brace 110, and the other end is connected to the winding mechanism of the harness tension portion 112. The winding mechanism of the harness tension portion 112 winds and unwinds the harness wire 111 by turning on and off a motor (not shown). With such a configuration, when the trainee 900 is about to fall, the fall prevention harness device winds up the harness wire 111 in accordance with the instruction of the overall control unit 210 that detects the movement, supports the upper body of the trainee 900 with the brace 110, and suppresses the trainee 900 from falling.

The brace 110 includes a posture sensor 217 for detecting the posture of the trainee 900. The posture sensor 217 is, for example, a combination of a gyro sensor and an acceleration sensor, and outputs an inclination angle of the abdomen on which the brace 110 is attached with respect to the direction of gravity.

The management monitor 139 is a display input device mainly for monitoring and operation by the training staff 901, and is attached to the frame 130. The management monitor 139 is, for example, a liquid crystal panel, and a touch panel is provided on the surface thereof. The management monitor 139 displays various menu items related to training settings, various parameter values at the time of training, training results, and the like. Further, an emergency stop button 232 is provided near the management monitor 139. When the training staff 901 presses the emergency stop button 232, an emergency stop of the walking training device 100 is performed.

The walking assist device 120 is attached to the affected leg of the trainee 900 and assists the trainee 900 in walking by reducing the load of extension and bending at the knee joint of the affected leg. The walking assist device 120 transmits data on the leg movement acquired through walking training to the overall control unit 210, or drives the joint portion in accordance with the instruction from the overall control unit 210. The walking assist device 120 can also be connected to a hip joint (a connecting member including a rotating portion) attached to the brace 110 that is a part of the fall prevention harness device via a wire or the like.

Details of Walking Assist Device 120

Figure 3:
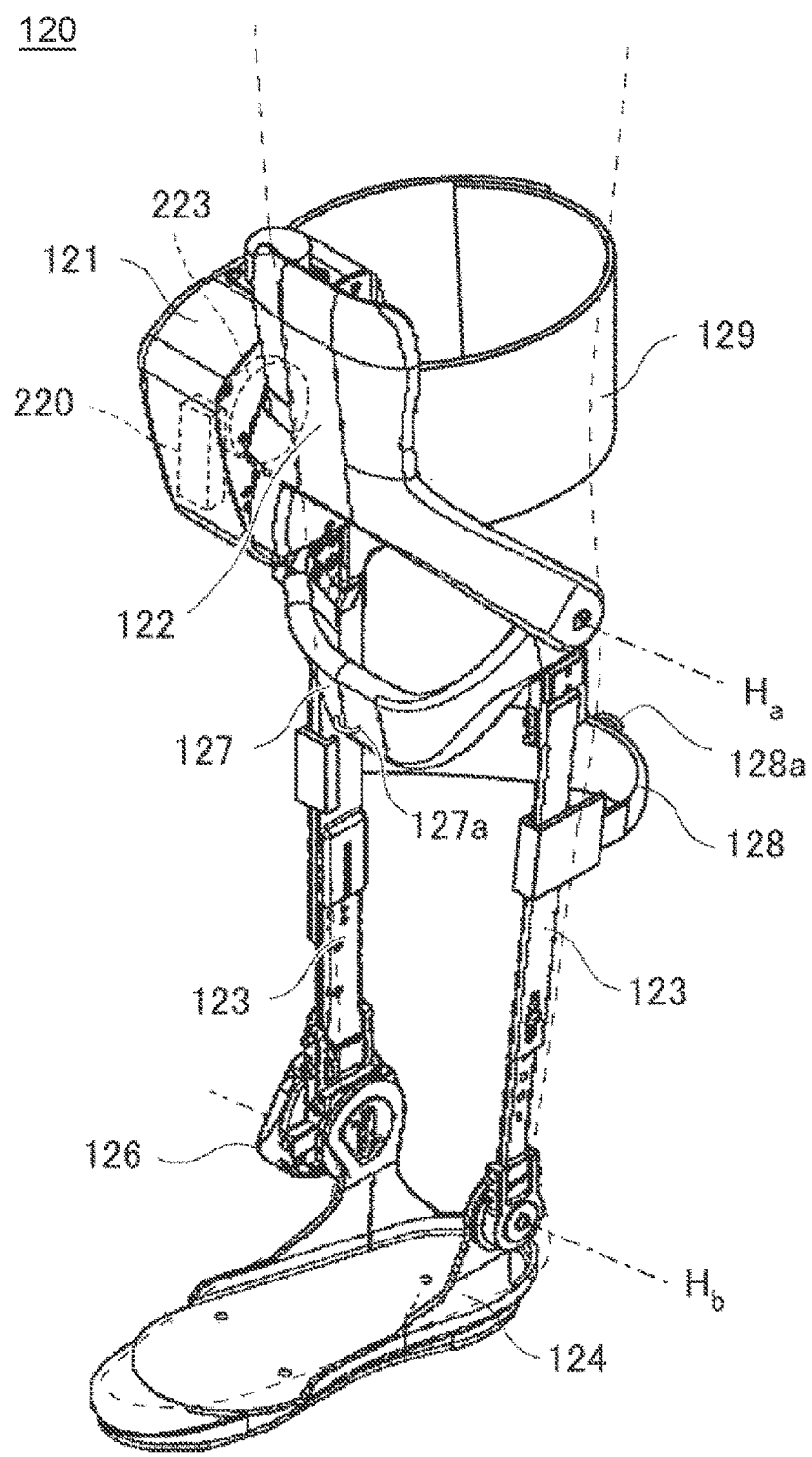
FIG. 3 is a schematic perspective view showing a configuration example of a walking assist device provided in the walking training device shown in FIG. 1.

FIG. 3 is a schematic perspective view showing a configuration example of the walking assist device 120. The walking assist device 120 mainly includes a control unit 121 and a plurality of frames that supports various parts of the affected leg. The walking assist device 120 is also referred to as a leg robot.

The control unit 121 includes an auxiliary control unit 220 that controls the walking assist device 120, and also includes a motor (not shown) that generates a driving force for assisting the extension motion and the bending motion of the knee joint. The frames that support various parts of the affected leg include an upper leg frame 122 and lower leg frames 123 that are pivotably connected to the upper leg frame 122. Further, the frames include a foot flat frame 124 pivotably connected to the lower leg frames 123, a front connecting frame 127 for connecting the front wire 134, and a rear connecting frame 128 for connecting the rear wire 136.

The upper leg frame 122 and the lower leg frames 123 pivot relative to each other around a hinge axis $H_a$ shown in the figure. The motor of the control unit 121 rotates in accordance with the instruction of the auxiliary control unit 220 to force the upper leg frame 122 and the lower leg frames 123 to relatively open or close around the hinge axis $H_a$. The angle sensor 223 housed in the control unit 121 is, for example, a rotary encoder, and detects the angle formed by the upper leg frame 122 and the lower leg frames 123 around the hinge axis $H_a$. The lower leg frames 123 and the foot flat frame 124 pivot relative to each other around the hinge axis $H_b$ shown in the figure. The relative pivot angle range is adjusted in advance by an adjusting mechanism 126.

The front connecting frame 127 is provided so as to extend in the right-left direction on the front side of the upper leg and connect to the upper leg frame 122 at both ends. Further, the front connecting frame 127 is provided with a connecting hook 127a for connecting the front wire 134, near the center in the right-left direction. The rear connecting frame 128 is provided so as to extend in the right-left direction on the rear side of the lower leg and connect to the lower leg frames 123 extending in the up-down direction at both ends. Further, the rear connecting frame 128 is provided with a connecting hook 128a for connecting the rear wire 136, near the center in the right-left direction.

The upper leg frame 122 includes an upper leg belt 129. The upper leg belt 129 is a belt integrally provided on the upper leg frame, and is wrapped around the upper leg portion of the affected leg to fix the upper leg frame 122 to the upper leg portion. This suppresses the entire walking assist device 120 from shifting with respect to the legs of the trainee 900.

System Configuration Example of Walking Training Device 100

Figure 4:
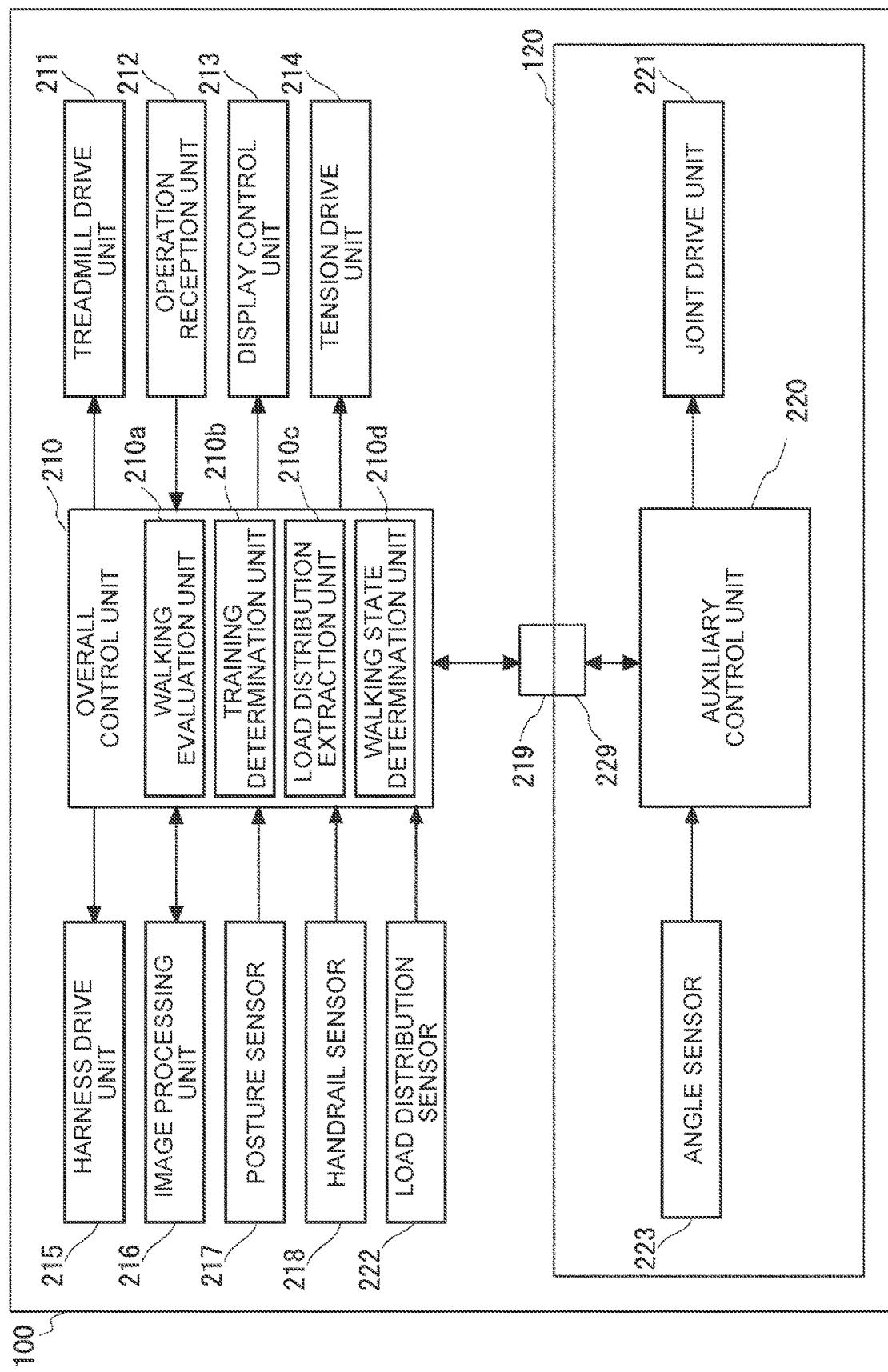
FIG. 4 is a block diagram showing a system configuration example of the walking training device shown in FIG. 1.

Subsequently, a system configuration example of the walking training device 100 will be described with reference to FIG. 4. FIG. 4 is a block diagram showing the system configuration example of the walking training device 100.

As shown in FIG. 4, the system configuration of the walking training device 100 includes the overall control unit 210, a treadmill drive unit 211, an operation reception unit 212, a display control unit 213, a harness drive unit 215, an image processing unit 216, the posture sensor 217, the handrail sensor 218, the load distribution sensor 222, a communication connection interface (IF) 219, and the walking assist device 120.

The overall control unit 210 is, for example, a micro processing unit (MPU), and executes control of the entire device by executing a control program read from a system memory.

The treadmill drive unit 211 includes a motor for rotating the belt 1311 of the treadmill 131 and a drive circuit thereof. The overall control unit 210 executes rotation control of the belt 1311 by transmitting a drive signal to the treadmill drive unit 211. The overall control unit 210 adjusts the rotation speed of the belt 1311 in accordance with, for example, the walking speed set by the training staff 901. Alternatively, the overall control unit 210 adjusts the rotation speed of the belt 1311 in accordance with the walking state of the trainee 900 determined based on the detection result of the load distribution sensor 222.

The operation reception unit 212 receives an input operation by the training staff 901 via an operation button provided on the device, a touch panel superimposed on the management monitor 139, an attached remote controller, or the like. The operation signal received by the operation reception unit 212 is transmitted to the overall control unit 210. The overall control unit 210 can give the instruction to switch on and off the power supply or give the instruction to start training based on the operation signal received by the operation reception unit 212. In addition, it is possible to input numerical values related to settings and select menu items. The operation reception unit 212 is not limited to the case where the input operation of the training staff 901 is received, and of course, the operation reception unit 212 can also receive the input operation of the trainee 900.

The display control unit 213 receives a display signal from the overall control unit 210, generates a display image, and displays the image on the training monitor 138 or the management monitor 139. The display control unit 213 generates an image showing the progress of training and a real-time image captured by the camera 140 in accordance with the display signal.

The tension drive unit 214 includes a motor for pulling the front wire 134 and a drive circuit thereof that are provided in the front tension portion 135, and a motor for pulling the rear wire 136 and a drive circuit thereof that are provided in the rear tension portion 137. The overall control unit 210 controls the winding of the front wire 134 and the winding of the rear wire 136 by transmitting a drive signal to the tension drive unit 214. Further, the overall control unit 210 controls the tensile force of each wire by controlling the driving torque of the motor, not limited to the winding operation. Further, the overall control unit 210 identifies the timing at which the affected leg switches from the standing state to the swinging state based on the detection result of the load distribution sensor 222, and increases or decreases the tensile force of each wire in synchronization with that timing, thereby assisting the forward swing motion of the affected leg.

The harness drive unit 215 includes a motor for pulling the harness wire 111 and a drive circuit thereof that are provided in the harness tension portion 112. The overall control unit 210 controls the winding of the harness wire 111 and the tensile force of the harness wire 111 by transmitting a drive signal to the harness drive unit 215. For example, when the trainee 900 is predicted to fall, the overall control unit 210 winds up the harness wire 111 by a certain amount to suppress the trainee from falling.

The image processing unit 216 is connected to the camera 140 and can receive an image signal from the camera 140. The image processing unit 216 receives an image signal from the camera 140 and performs image processing on the received image signal to generate image data, in accordance with the instruction from the overall control unit 210. Further, the image processing unit 216 can also perform image processing on the image signal received from the camera 140 to execute a specific image analysis, in accordance with the instruction from the overall control unit 210. For example, the image processing unit 216 detects the position of the foot (standing position) of the affected leg that is in contact with the treadmill 131 by image analysis. Specifically, for example, the standing position is calculated by extracting an image region near the tip of the foot flat frame 124 and analyzing an identification marker drawn on the belt 1311 that overlaps the tip portion.

As described above, the posture sensor 217 detects the inclination angle of the abdomen of the trainee 900 with respect to the direction of gravity, and transmits the detection signal to the overall control unit 210. The overall control unit 210 calculates the posture of the trainee 900, specifically the inclination angle of the trunk of the body, using the detection signal from the posture sensor 217. The overall control unit 210 and the posture sensor 217 may be connected by wire or by short-range wireless communication.

The handrail sensor 218 detects a load applied to the handrail 130a. That is, a load corresponding to a portion of the weight of the trainee 900 that the trainee 900 cannot support with both legs is applied to the handrail 130a. The handrail sensor 218 detects this load and transmits a detection signal to the overall control unit 210.

As described above, the load distribution sensor 222 detects the magnitude and the distribution of the surface pressure (load) received from the sole of the trainee 900 and transmits the detection signal to the overall control unit 210. The overall control unit 210 receives and analyzes the detection signal to determine the walking state and estimate switching.

The overall control unit 210 also plays a role as a function execution unit that executes various calculations related to the control and performs the control. The overall control unit 210 includes, for example, a walking evaluation unit 210a, a training determination unit 210b, a load distribution extraction unit 210c, and a walking state determination unit 210d. The load distribution extraction unit 210c and the walking state determination unit 210d will be described later.

The walking evaluation unit 210a evaluates whether the walking motion of the trainee 900 is abnormal walking using the data acquired from various sensors. The training determination unit 210b determines the training result for a series of walking trainings based on, for example, the cumulative number of abnormal walking evaluated by the walking evaluation unit 210a.

The method of determining the training result and the criteria for determining the training result may be set as appropriate. For example, the training result may be determined by comparing the amount of movement of the paralyzed body portion with the reference for each walking phase. The walking phase is obtained by dividing one walking cycle for the affected leg (or a healthy leg) into a standing phase in which the leg is in the standing state, a transition phase from the standing phase to a swinging phase in which the leg is in the swinging state, a swinging phase, a transition phase from the swinging phase to the standing phase, and so on. The walking phase can be classified (determined) based on, for example, the detection result by the load distribution sensor 222. As described above, for the walking cycle, one cycle can be regarded as including the standing phase, the transition phase, the swinging phase, and the transition phase. However, it does not matter which phase is defined as the start phase. In addition, for the walking cycle, one cycle can be regarded as including, for example, a both leg-supported state, a single leg-(affected leg-) supported state, the both leg-supported state, and a single leg-(healthy leg-) supported state, and in this case, it does not matter which state is defined as the starting state.

In addition, the walking cycle focusing on the right leg or the left leg (healthy leg or affected leg) can be further divided, and can be represented by dividing the standing phase into an initial ground contact and four phases and dividing the swinging phase into three phases. The initial ground contact refers to a moment when an observed foot contacts the floor, and the four phases of the standing phase refer to a load response phase, a standing middle phase, a standing end phase, and a pre-swinging phase. The load response phase is the phase from the initial ground contact to the moment when the foot on the opposite side leaves the floor (contralateral takeoff). The standing middle phase is the phase from the contralateral takeoff to the moment when the heel of the observed foot leaves the floor (heel takeoff). The standing end phase is the phase from the heel takeoff to the initial ground contact on the opposite side. The pre-swinging phase is the phase from the initial ground contact on the opposite side to the time when the observed foot leaves the floor (takeoff). The three phases of the swinging phase refer to a swinging initial phase, a swinging middle phase, and a swinging end phase. The swinging initial phase is the phase from the end of the pre-swinging phase (the above-mentioned takeoff) to the time when both feet cross (feet crossing). The swinging middle phase is the phase from the time when the feet cross to the time when the shinbone becomes vertical (vertical shinbone). The swinging end phase is the phase from the time when the shinbone is vertical to the next initial ground contact.

The communication connection IF 219 is an interface connected to the overall control unit 210, and is an interface for providing a command to the walking assist device 120 attached to the affected leg of the trainee 900 and receiving sensor information.

The walking assist device 120 can include a communication connection IF 229 that is connected to the communication connection IF 219 by a wire or wirelessly. The communication connection IF 229 is connected to the auxiliary control unit 220 of the walking assist device 120. The communication connection IF 219 and the communication connection IF 229 are communication interfaces such as a wired local area network (LAN) or a wireless LAN conforming to the communication standards.

Further, the walking assist device 120 can include the auxiliary control unit 220, a joint drive unit 221, and the angle sensor 223. The auxiliary control unit 220 is, for example, an MPU, and controls the walking assist device 120 by executing the control program provided by the overall control unit 210. Further, the auxiliary control unit 220 notifies the overall control unit 210 of the state of the walking assist device 120 via the communication connection IF 219 and the communication connection IF 229. Further, the auxiliary control unit 220 receives a command from the overall control unit 210 and executes control of starting, stopping, and the like of the walking assist device 120.

The joint drive unit 221 includes a motor of the control unit 121 and a drive circuit thereof. The auxiliary control unit 220 transmits the drive signal to the joint drive unit 221 to force the upper leg frame 122 and the lower leg frames 123 to relatively open or close around the hinge axis $H_a$. Such motions assist the knee extension and bending motions and suppress knee collapse.

As described above, the angle sensor 223 detects the angle formed by the upper leg frame 122 and the lower leg frames 123 around the hinge axis $H_a$, and transmits the detection signal to the auxiliary control unit 220. The auxiliary control unit 220 receives this detection signal and calculates the opening angle of the knee joint.

The response performance of the load distribution sensor 222 when the load distribution sensor 222 is unloaded is usually lower than the response performance when the load distribution sensor 222 is loaded. Therefore, when the load distribution received from the sole of the trainee 900 moves with the rotation (movement) of the belt 1311, not only the load distribution after the movement is detected but also the load distribution before the movement is unintentionally detected without being removed. Therefore, if no measures are taken, the overall control unit 210 cannot accurately determine the walking state of the trainee 900. As a result, the trainee 900 cannot perform effective walking training.

Figure 5:
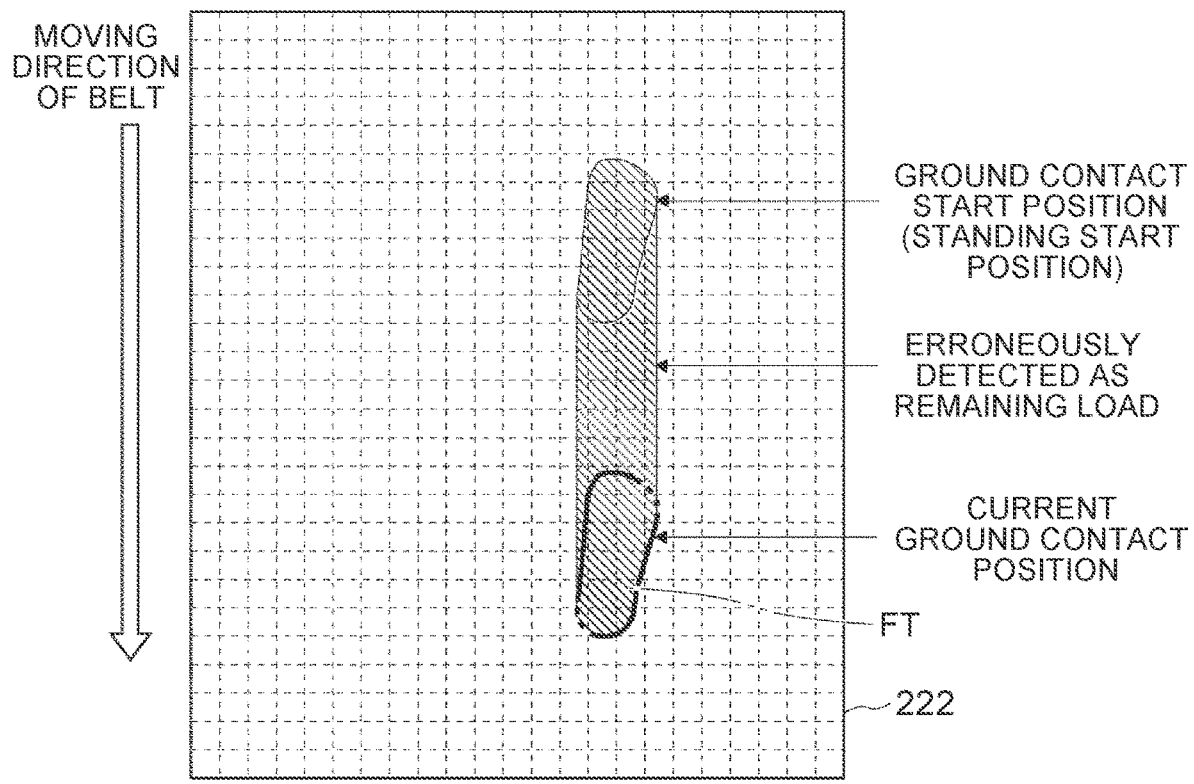
FIG. 5 is a schematic plan view illustrating an influence of an unintended load distribution detected by a load distribution sensor.

FIG. 5 is a schematic plan view illustrating an influence of an unintended load distribution detected by the load distribution sensor 222. In the example of FIG. 5, with the movement of the belt 1311, the ground contact region of the sole FT of the right leg moves from the standing start position to the moving direction of the belt 1311. The response performance of the load distribution sensor 222 when the load distribution sensor 222 is unloaded is low. Therefore, not only the ground contact region of the (current) sole FT after movement is detected, but also the load distribution in the ground contact region of the sole FT before movement (that is, the ground contact region of the sole FT from the standing start position to the present time) is unintentionally detected without being removed.

Thus, in the present embodiment, the load distribution that is detected unintentionally due to the low response performance of the load distribution sensor 222 is excluded from the load distribution detected by the load distribution sensor 222 using the load distribution extraction unit 210*c* and the walking state determination unit 210*d*, so that the accuracy of determining the walking state of the trainee 900 is improved.

Specifically, first, the load distribution extraction unit 210*c* extracts the load distribution in the region corresponding to the position of the sole of the trainee 900 during walking training, out of the load distribution detected by the load distribution sensor 222. The region corresponding to the position of the sole of the trainee 900 is determined based on, for example, the size (area, length, width, and the like) of the sole of the trainee 900 registered in the database through an input operation or the like. Alternatively, the region corresponding to the position of the sole of the trainee 900 is determined based on the shape of the sole of the trainee 900 registered in the database through an input operation or the like (including the shape of the sole of the shoe worn by the trainee 900). After that, the walking state determination unit 210*d* determines the walking state of the trainee 900 (for example, the timing of switching from the standing state to the swinging state) based on the load distribution extracted by the load distribution extraction unit 210*c*.

Example of Method of Determining Walking State of Trainee 900

Figure 6:
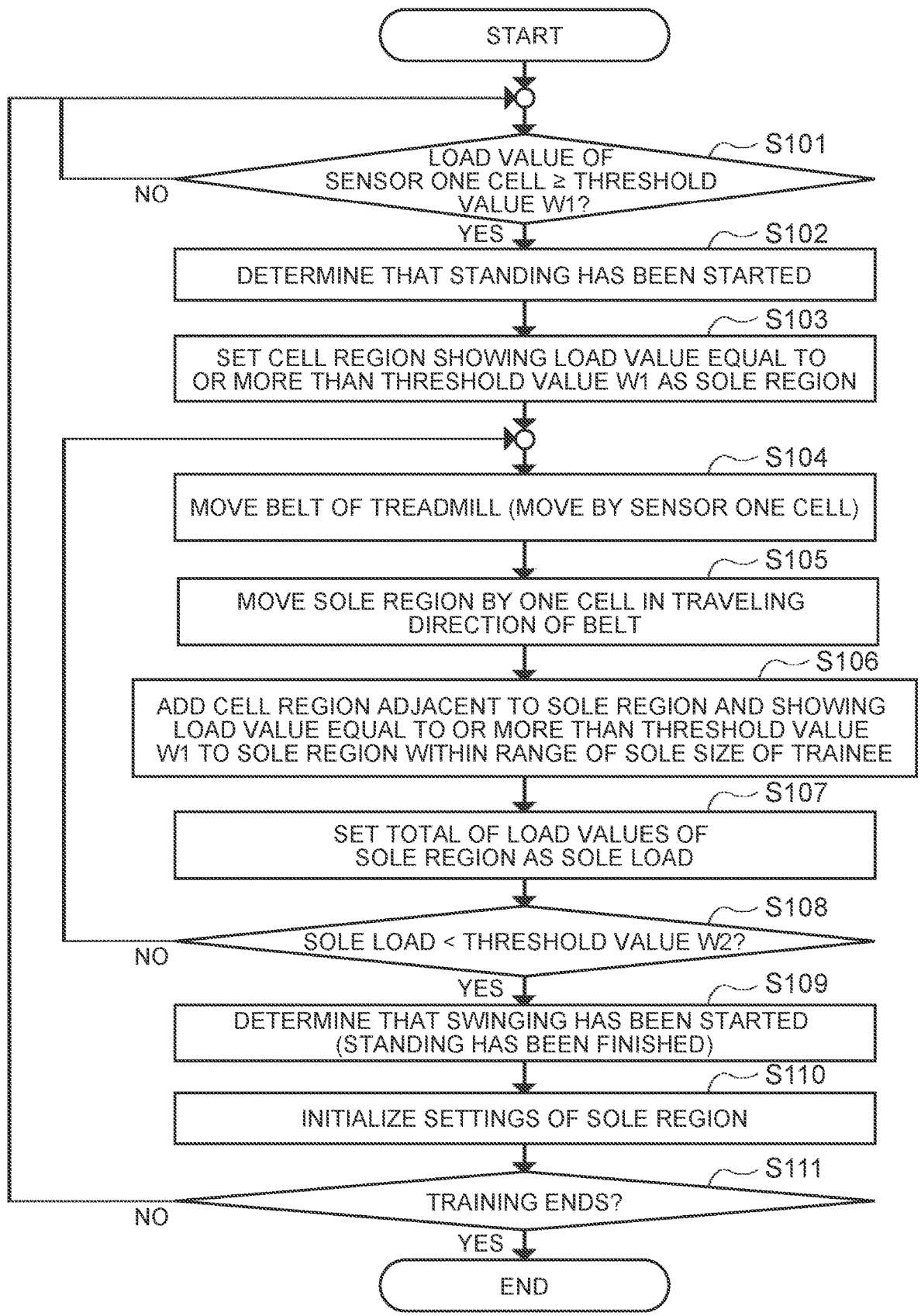
FIG. 6 is a flowchart showing an example of a method of determining the walking state of the trainee by the walking training device shown in FIG. 1.
Figure 7:
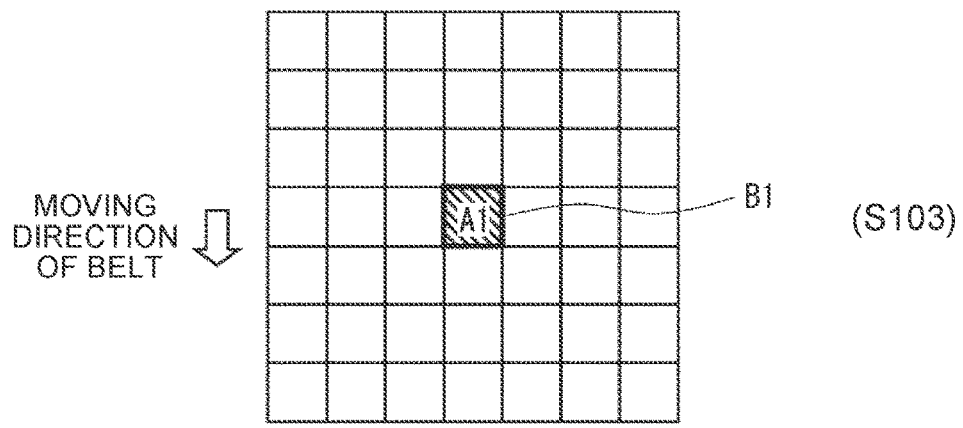
FIG. 7 is a diagram illustrating the example of the method of determining the walking state of the trainee by the walking training device shown in FIG. 1.
Figure 7:
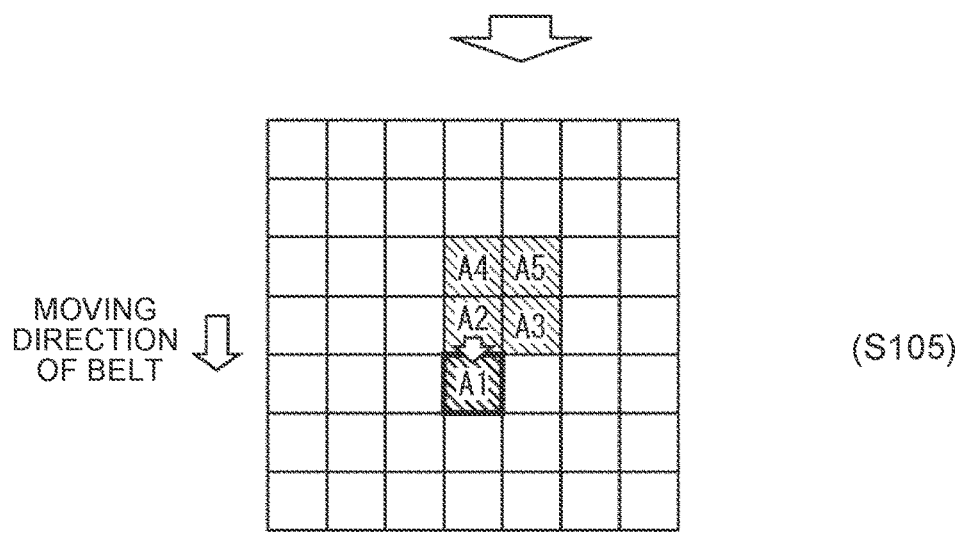
Figure 7:
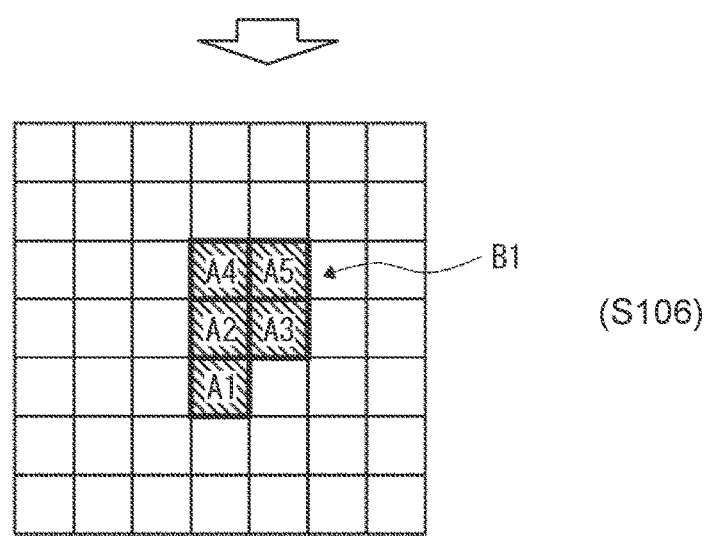

FIG. 6 is a flowchart showing an example of a method of determining the walking state of the trainee 900 by the walking training device 100. Further, FIG. 7 is a diagram illustrating the example of the method of determining the walking state of the trainee 900 by the walking training device 100. In the following, the method of determining the walking state from the start of standing to the end of standing of the right leg will be mainly described.

First, it is determined whether the load value of at least one sensor, of the plurality of sensors (cells) constituting the load distribution sensor 222, other than the sensor that receives the load from the left leg is equal to or more than a threshold value W1 (step S101).

For example, when the load values of all the sensors, of the sensors constituting the load distribution sensor 222, other than the sensor that receives the load from the left leg are less than the threshold value W1 (NO in step S101), the walking training device 100 waits until the load value of at least one sensor becomes equal to or more than the threshold value W1.

When the load value of at least one sensor, of the sensors (cells) constituting the load distribution sensor 222, other than the sensor that receives the load from the left leg becomes equal to or more than the threshold value W1 (YES in step S101), it is determined that the right leg has transitioned from the swinging state to the standing state (that is, the right leg has started standing) (step S102).

When it is determined that the right leg has started standing, a region (cell region) of the sensor, of the sensors constituting the load distribution sensor 222, other than the sensor that receives the load from the left leg and showing the load value equal to or more than the threshold value W1 is set as a sole region B1 of the right leg (step S103). In the example of FIG. 7, a region (cell region) A1 corresponding to one sensor is set as the sole region B1 of the right leg (step S103).

After that, the belt 1311 of the treadmill 131 moves by one sensor (one cell) (step S104). Along with this, the load distribution by the load distribution sensor 222 also moves, so that the sole region B1 of the right leg is moved by one cell in the traveling direction of the belt 1311 (step S105).

At this time, the region (cell region) of the sensor adjacent to the sole region B1 and showing the load value equal to or more than the threshold value W1 is newly added as the sole region B1 within the range of the size (area, length, width, and the like) of the sole of the trainee 900 (step S106). In the example of FIG. 7, the area of the sole of the right leg of the trainee 900 is registered in advance in the database as the area of five sensors. Therefore, in the example of FIG. 7, the regions (cell regions) A2 to A5 of the four sensors adjacent to the cell region A1 are newly added as the sole region B1 of the right leg (step S106).

At this time, the total of the load values of the five sensors constituting the sole region B1 is set as the load value (sole load) received from the sole of the right leg (step S107). On the other hand, the load values of the sensors other than the five sensors are not used as the load value received from the sole of the right leg.

That is, here, the load distribution extraction unit 210*c* provided in the overall control unit 210 extracts the load distribution of the region corresponding to the position of the sole of the right leg of the trainee 900, out of the load distribution detected by the load distribution sensor 222. More specifically, the load distribution extraction unit 210*c* extracts the load distribution within the range of the size of the sole of the trainee 900, such that the extracted load distribution includes a load at the rear end of the load distribution extending in the moving direction of the belt 1311, out of the load distribution detected by the load distribution sensor 222.

After that, during the period in which the sole load of the right leg (total load of the sole region B1) shows a value equal to or more than the threshold value W2 (NO in step S108), the processes of steps S104 to S107 are repeated.

When the sole load of the right leg shows a value less than the threshold value W2 (YES in step S108), it is determined that the right leg has transitioned from the standing state to the swinging state (that is, the right leg has finished standing) (step S109). When it is determined that the right leg has finished standing, the settings of the sole region B1 of the right leg are initialized (step S110).

That is, here, the walking state determination unit 210*d* provided in the overall control unit 210 determines the walking state of the trainee 900 (for example, transition from the standing state to the swinging state of the right leg) based on the load distribution extracted by the load distribution extraction unit 210*c*.

After that, when the training is continued (NO in step S111), the walking state from the start of standing to the end of standing of the left leg, which is the opposite leg, is determined. The walking state from the start of standing to the end of standing of the right leg is determined based only on the load received from the right leg, among the loads received from the right leg and the left leg, while the walking state from the start of standing to the end of standing of the left leg is determined based only on the load received from the left leg, among the loads received from the right leg and the left leg.

When the training ends after the predetermined training time has elapsed (YES in step S111), for example, the determination of the walking state ends.

Thus, the walking training device 100 according to the present embodiment extracts the load distribution within the range of the size of the sole of the trainee 900, such that the extracted load distribution includes the load at the rear end of the load distribution extending in the moving direction of the belt 1311, out of the load distribution detected by the load distribution sensor 222, and determines the walking state of the trainee 900 based on the extracted load distribution. In other words, the walking training device 100 excludes, from the load distribution detected by the load distribution sensor 222, the load distribution that is detected unintentionally due to the low response performance of the load distribution sensor 222 when the load distribution sensor 222 is unloaded, to determine the walking state of the trainee 900. Thereby, the walking training device 100 can improve the accuracy of determining the walking state of the trainee 900, and as a result, it becomes possible to provide the trainee 900 with effective walking training.

Another Example of Method of Determining Walking State of Trainee 900

Figure 8:
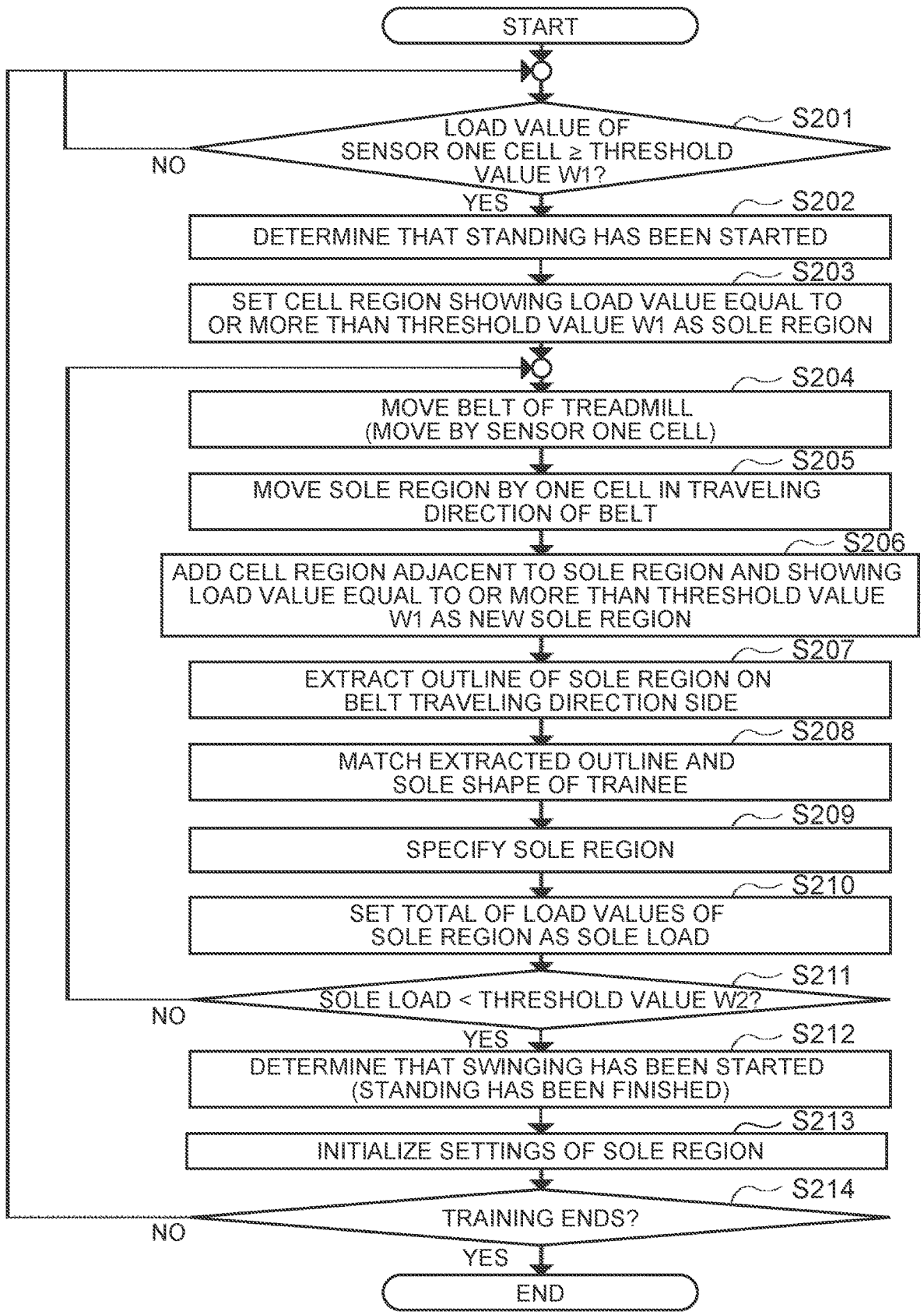
FIG. 8 is a flowchart showing another example of the method of determining the walking state of the trainee by the walking training device shown in FIG. 1.
Figure 9:
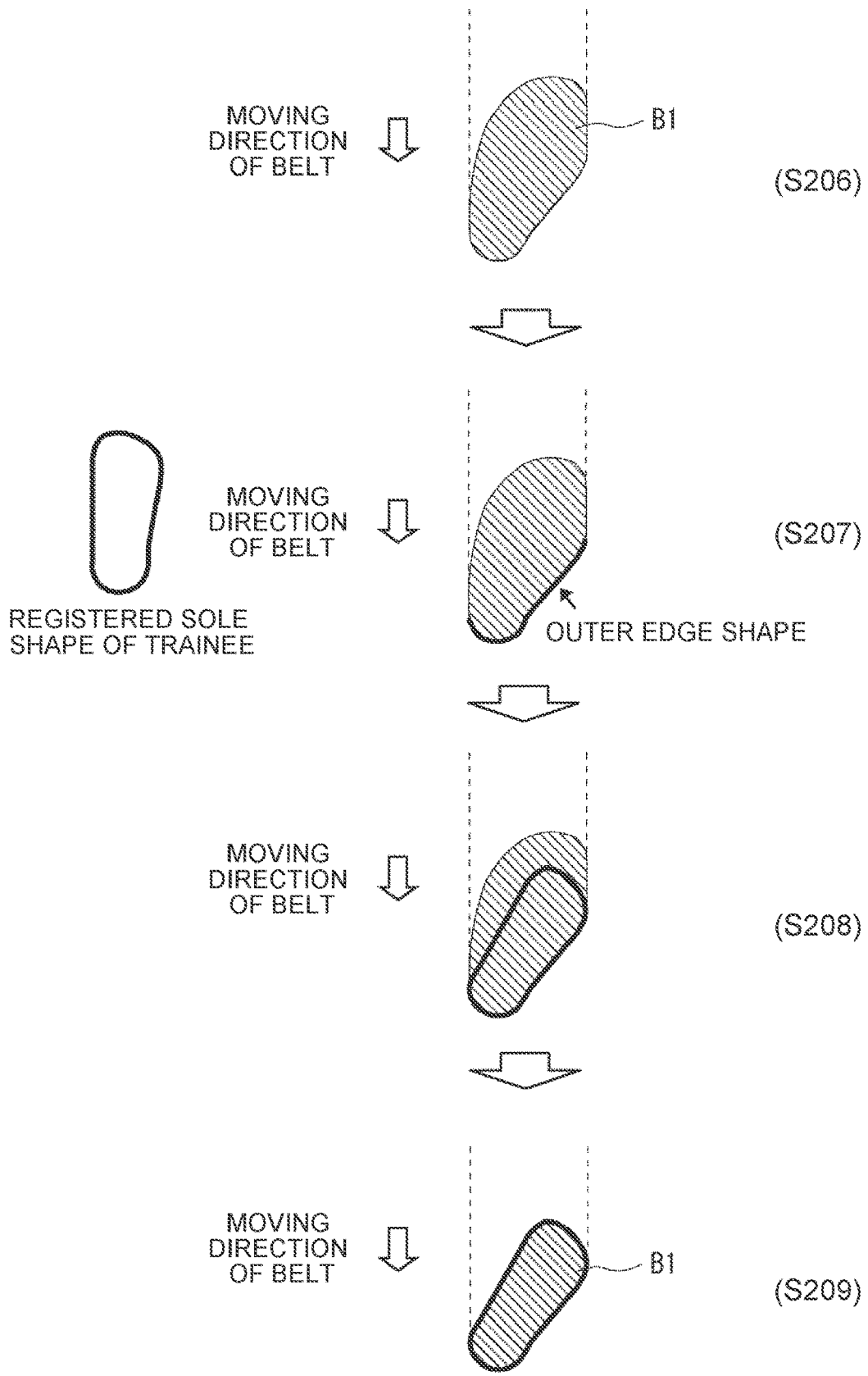
FIG. 9 is a diagram illustrating the other example of the method of determining the walking state of the trainee by the walking training device shown in FIG. 1.

FIG. 8 is a flowchart showing another example of the method of determining the walking state of the trainee 900 by the walking training device 100. Further, FIG. 9 is a diagram illustrating the other example of the method of determining the walking state of the trainee 900 by the walking training device 100. In the following, the method of determining the walking state from the start of standing to the end of standing of the right leg will be mainly described.

First, it is determined whether the load value of at least one sensor, of the plurality of sensors (cells) constituting the load distribution sensor 222, other than the sensor that receives the load from the left leg is equal to or more than the threshold value W1 (step S201).

For example, when the load values of all the sensors, of the sensors constituting the load distribution sensor 222, other than the sensor that receives the load from the left leg are less than the threshold value W1 (NO in step S201), the walking training device 100 waits until the load value of at least one sensor becomes equal to or more than the threshold value W1.

When the load value of at least one sensor, of the sensors (cells) constituting the load distribution sensor 222, other than the sensor that receives the load from the left leg becomes equal to or more than the threshold value W1 (YES in step S201), it is determined that the right leg has transitioned from the swinging state to the standing state (that is, the right leg has started standing) (step S202).

When it is determined that the right leg has started standing, a region (cell region) of a sensor, of the sensors constituting the load distribution sensor 222, showing the load value equal to or more than the threshold value W1 other than the sensor that receives the load from the left leg is set as the sole region B1 of the right leg (step S203).

After that, the belt 1311 of the treadmill 131 moves by one sensor (one cell) (step S204). Along with this, the load distribution by the load distribution sensor 222 also moves, so that the sole region B1 of the right leg is moved by one cell in the traveling direction of the belt 1311 (step S205).

At this time, a sensor region (cell region) adjacent to the sole region B1 and showing the load value equal to or more than the threshold value W1 is newly added as the sole region B1 (step S206).

After that, an outer edge shape of the rear end of the sole region B1 (in other words, the load distribution) extending in the moving direction of the belt 1311 is extracted (step S207).

After that, the extracted outer edge shape and the shape of the sole of the trainee 900 registered in advance in the database are matched (step S208). Specifically, part of the shape of the sole of the trainee 900 registered in advance in the database is matched with the extracted outer edge shape. Thereby, the position of the sole of the trainee 900 is specified. The position of the sole of the trainee 900 specified by matching is set as a new sole region B1 (step S209).

At this time, the total of the load values of the sensors constituting the sole region B1 is set as the load value (sole load) received from the sole of the right leg (step S210). On the other hand, the load values of the sensors other than those sensors are not used as the load value received from the sole of the right leg.

That is, here, the load distribution extraction unit 210c provided in the overall control unit 210 specifies the position of the sole of the trainee 900 from the outer edge shape at the rear end of the load distribution extending in the moving direction of the belt 1311, and extracts the load distribution in the region corresponding to the specified position of the sole.

After that, during the period in which the sole load of the right leg (total load of the sole region B1) shows a value equal to or more than the threshold value W2 (NO in step S211), the processes of steps S204 to S210 are repeated.

When the sole load of the right leg shows a value less than the threshold value W2 (YES in step S211), it is determined that the right leg has transitioned from the standing state to the swinging state (that is, the right leg has finished standing) (step S212). When it is determined that the right leg has finished standing, the settings of the sole region B1 of the right leg are initialized (step S213).

That is, here, the walking state determination unit 210d provided in the overall control unit 210 determines the walking state of the trainee 900 (for example, transition from the standing state to the swinging state of the right leg) based on the load distribution extracted by the load distribution extraction unit 210c.

After that, when the training is continued (NO in step S214), the walking state from the start of standing to the end of standing of the left leg, which is the opposite leg, is then determined. The walking state from the start of standing to the end of standing of the right leg is determined based only on the load received from the right leg, among the loads received from the right leg and the left leg, while the walking state from the start of standing to the end of standing of the left leg is determined based only on the load received from the left leg, among the loads received from the right leg and the left leg.

When the training ends after the predetermined training time has elapsed (YES in step S214), for example, the determination of the walking state ends.

Thus, the walking training device 100 according to the present embodiment specifies the position of the sole of the trainee 900 from the outer edge shape at the rear end of the load distribution extending in the moving direction of the belt 1311, and determines the walking state of the trainee 900 based on the load distribution at the specified position of the sole. In other words, the walking training device 100 excludes, from the load distribution detected by the load distribution sensor 222, the load distribution that is detected unintentionally due to the low response performance of the load distribution sensor 222 when the load distribution sensor 222 is unloaded, to determine the walking state of the trainee 900. Thereby, the walking training device 100 can improve the accuracy of determining the walking state of the trainee 900, and as a result, it becomes possible to provide the trainee 900 with effective walking training.

The specification of the position of the sole of the trainee 900 is not limited to the method described above, and for example, an image captured by the camera 140 (imaging device) may be further used.

Further, in each of the above embodiments, the case where the area of the sole of each leg of the trainee 900 corresponds to the area of five sensors has been described as an example, but the present disclosure is not limited to this. The area of the sole of each leg of the trainee 900 can be set as appropriate. Further, by registering the length and the width of the sole of each leg of the trainee 900, it is possible to set an upper limit value for the length and the width of the sole region B1 extracted by the load distribution extraction unit 210c.

Further, in each of the above embodiments, the case where the trainee 900 is a hemiplegic patient suffering from paralysis in one leg has been described as an example, but the present disclosure is not limited to this. The trainee 900 may be, for example, a patient suffering from paralysis of both legs. In that case, the trainee 900 performs training while wearing the walking assist device 120 on both legs. Alternatively, the trainee 900 does not have to wear the walking assist device 120 on any of the legs.

Further, in each of the above embodiments, the present disclosure has been described as a hardware configuration. However, the present disclosure is not limited thereto. In the present disclosure, the control of the walking training device 100 can be realized by causing a central processing unit (CPU) to execute a computer program.

The above-mentioned program can be stored and supplied to a computer using various types of non-transitory computer-readable media. The non-transitory computer-readable media include various types of tangible storage media. The non-transitory computer-readable media include, for example, a magnetic recording medium, an opto-magnetic recording medium, a compact disc read only memory (CD-ROM), a compact disc recordable (CD-R), a compact disc rewritable (CD-R/W), and a semiconductor memory. The magnetic recording medium is, for example, a flexible disk, a magnetic tape, a hard disk drive, and the like. The opto-magnetic recording medium is, for example, an opto-magnetic disk. The semiconductor memory is, for example, a mask ROM, a programmable rom (PROM), an erasable PROM (EPROM), a flash ROM, a random access memory (RAM), and the like. Further, the program may be supplied to the computer using various types of transitory computer-readable media. Examples of the transitory computer-readable media include electrical signals, optical signals, and electromagnetic waves. The transitory computer-readable media can supply the program to the computer via a wired communication path such as an electric wire and an optical fiber, or a wireless communication path.

What is claimed is:

1. A walking training system comprising:
a treadmill;
a load distribution sensor that is provided on a lower side of a belt of the treadmill so as not to move together with the belt and that detects a distribution of a load received from a sole of a trainee riding on the belt of the treadmill, wherein
the load distribution sensor comprises a plurality of sensors arranged in a matrix on the lower side of the belt,
the plurality of sensors comprises a region set as a sole region, and the sensors that receive a load from a left leg and showing a load value equal to or greater than a first threshold value are set as the sole region,
the sole region is moved in a traveling direction of the belt along with movement of the belt
a region adjacent to the set sole region and receiving a load equal to or greater than the first threshold value is newly set as the sole region, and
the sole region is set so that a size of the sole region is equal to or smaller than a size of the sole of the trainee, the size of a sole of the trainee being stored in advance in a database;
an extraction unit that extracts a load distribution in a region corresponding to a position of the sole of the trainee during walking training, out of a load distribution detected by the load distribution sensor; and
a determination unit that determines a walking state of the trainee based on the load distribution extracted by the extraction unit.

2. The walking training system according to claim 1, wherein the extraction unit extracts a load distribution in a range of a sole size of the trainee, out of the load distribution detected by the load distribution sensor, the extracted load distribution including a load at a rear end of a load distribution extending in a moving direction of the belt of the treadmill.

3. The walking training system according to claim 2, wherein the sole size of the trainee includes at least one of an area, a length, and a width of the sole and is registered in advance in a database.

4. The walking training system according to claim 1, wherein the extraction unit specifies the position of the sole of the trainee from an outer edge shape at a rear end of a load distribution extending in a moving direction of the belt of the treadmill, and extracts a load distribution in a region corresponding to the specified position of the sole.

5. The walking training system according to claim 4, wherein the extraction unit specifies the position of the sole of the trainee during walking training by matching part of a shape of the sole of the trainee registered in advance in a database with the outer edge shape.

6. The walking training system according to claim 1, further comprising an imaging device for capturing an image of the trainee during walking training, wherein the extraction unit specifies the position of the sole of the trainee during walking training from the image captured by the imaging device, and extracts a load distribution in a region corresponding to the specified position of the sole.

7. A method for controlling a walking training system, the method comprising:
a step of using a load distribution sensor that is provided on a lower side of a belt of a treadmill so as not to move together with the belt, to detect a distribution of a load received from a sole of a trainee riding on the belt of the treadmill, wherein
the load distribution sensor comprises a plurality of sensors arranged in a matrix on the lower side of the belt, the plurality of sensors comprises a region set as a sole region, and the sensors that receive a load from a left leg and showing a load value equal to or greater than a first threshold value are set as the sole region, the sole region is moved in a traveling direction of the belt along with movement of the belt a region adjacent to the set sole region and receiving a load equal to or greater than the first threshold value is newly set as the sole region, and the sole region is set so that a size of the sole region is equal to or smaller than a size of a sole of the trainee, the size of a sole of the trainee being stored in advance in a database;

a step of extracting a load distribution in a region corresponding to a position of the sole of the trainee during walking training, out of a load distribution detected by the load distribution sensor; and a step of determining a walking state of the trainee based on the extracted load distribution.

8. A non-transitory storage medium storing instructions that are executable by one or more processors to perform functions comprising:

a process of using a load distribution sensor that is provided on a lower side of a belt of a treadmill so as not to move together with the belt, to detect a distribution of a load received from a sole of a trainee riding on the belt of the treadmill, wherein the load distribution sensor comprises a plurality of sensors arranged in a matrix on the lower side of the belt, the plurality of sensors comprises a region set as a sole region, and the sensors that receive a load from a left leg and showing a load value equal to or greater than a first threshold value are set as the sole region, the sole region is moved in a traveling direction of the belt along with movement of the belt a region adjacent to the set sole region and receiving a load equal to or greater than the first threshold value is newly set as the sole region, and the sole region is set so that a size of the sole region is equal to or smaller than a size of a sole of the trainee, the size of a sole of the trainee being stored in advance in a database;

a process of extracting a load distribution in a region corresponding to a position of the sole of the trainee during walking training, out of a load distribution detected by the load distribution sensor; and a process of determining a walking state of the trainee based on the extracted load distribution.

\* \* \* \* \*